United States Patent
Aribert et al.

(10) Patent No.: US 11,993,559 B2
(45) Date of Patent: May 28, 2024

(54) METHOD FOR TREATING AN ALCOHOL FEEDSTOCK FOR THE PRODUCTION OF OLEFINS

(71) Applicants: TOTAL RESEARCH & TECHNOLOGY FELUY, Seneffe (BE); IFP Energies Nouvelles, Rueil-Malmaison (FR)

(72) Inventors: Nicolas Aribert, Rueil-Malmaison (FR); Ludovic Chahen, Rueil-Malmaison (FR); Arnaud Lanoue, Rueil-Malmaison (FR); Vincent Coupard, Rueil-Malmaison (FR); Nikolai Nesterenko, Nivelle (BE)

(73) Assignees: TOTAL RESEARCH & TECHNOLOGY FELUY, Seneffe (BE); IFP Energies Nouvelies, Rueil-Malmaison (FR)

( * ) Notice: Subject to any disclaimer, the term of this patent is extended or adjusted under 35 U.S.C. 154(b) by 506 days.

(21) Appl. No.: 17/415,910

(22) PCT Filed: Nov. 27, 2019

(86) PCT No.: PCT/EP2019/082776
§ 371 (c)(1),
(2) Date: Jun. 18, 2021

(87) PCT Pub. No.: WO2020/126374
PCT Pub. Date: Jun. 25, 2020

(65) Prior Publication Data
US 2022/0064088 A1    Mar. 3, 2022

(30) Foreign Application Priority Data

Dec. 20, 2018  (FR) ..................... 1873651

(51) Int. Cl.
*C07C 29/80*  (2006.01)
*B01D 3/00*  (2006.01)
(Continued)

(52) U.S. Cl.
CPC .............. *C07C 29/80* (2013.01); *B01D 3/001* (2013.01); *B01D 3/007* (2013.01); *B01D 3/009* (2013.01);
(Continued)

(58) Field of Classification Search
CPC ................................................. C07C 29/74–94
See application file for complete search history.

(56) References Cited

U.S. PATENT DOCUMENTS 2,910,412 A    10/1959  Muller et al.
9,085,502 B2    7/2015  Coupard et al.
(Continued)

FOREIGN PATENT DOCUMENTS

FR    2978145 A1    1/2013
FR    2998567 A1    5/2014
(Continued)

OTHER PUBLICATIONS

International Search Report PCT/EP2019/082776 dated Feb. 24, 2020 (pp. 1-3).

*Primary Examiner* — Medhanit W Bahta
(74) *Attorney, Agent, or Firm* — Millen, White, Zelano & Branigan, P.C.; Brion P. Heaney

(57) ABSTRACT

The invention relates to a process for treating an alcoholic feedstock, comprising: a) a stage of preheating of said alcoholic feedstock to a temperature of between 70° C. and 200° C.; b) a stage of pretreatment on an acidic solid, operating at a temperature of between 70° C. and 200° C., to produce a pretreated alcoholic feedstock; c) a stage of partial vaporization to produce a vaporized stream and a
(Continued)

liquid stream; and d) a stage of purification of the liquid stream resulting from stage c), to give a stream rich in water, a stream rich in monoalcohol and a stream rich in impurities.

21 Claims, 1 Drawing Sheet

(51) Int. Cl.
*B01D 3/06* (2006.01)
*B01D 3/14* (2006.01)
*B01D 3/40* (2006.01)
*C07C 29/88* (2006.01)

(52) U.S. Cl.
CPC ............... *B01D 3/06* (2013.01); *B01D 3/148* (2013.01); *B01D 3/40* (2013.01); *C07C 29/88* (2013.01)

(56) References Cited

U.S. PATENT DOCUMENTS

| | | | |
|---|---|---|---|
| 9,242,914 B2 | 1/2016 | Minoux et al. | |
| 9,663,414 B2 | 5/2017 | Coupard et al. | |
| 9,725,376 B2 | 8/2017 | Coupard et al. | |
| 2013/0190547 A1* | 7/2013 | Coupard | ................... C07C 1/24 585/639 |
| 2014/0311889 A1* | 10/2014 | Zaher | ..................... B01D 3/002 203/77 |

FOREIGN PATENT DOCUMENTS

| | | |
|---|---|---|
| FR | 2998568 A1 | 5/2014 |
| GB | 2091260 A | 7/1982 |
| WO | 10060981 A1 | 6/2010 |
| WO | 13011208 A1 | 1/2013 |

\* cited by examiner

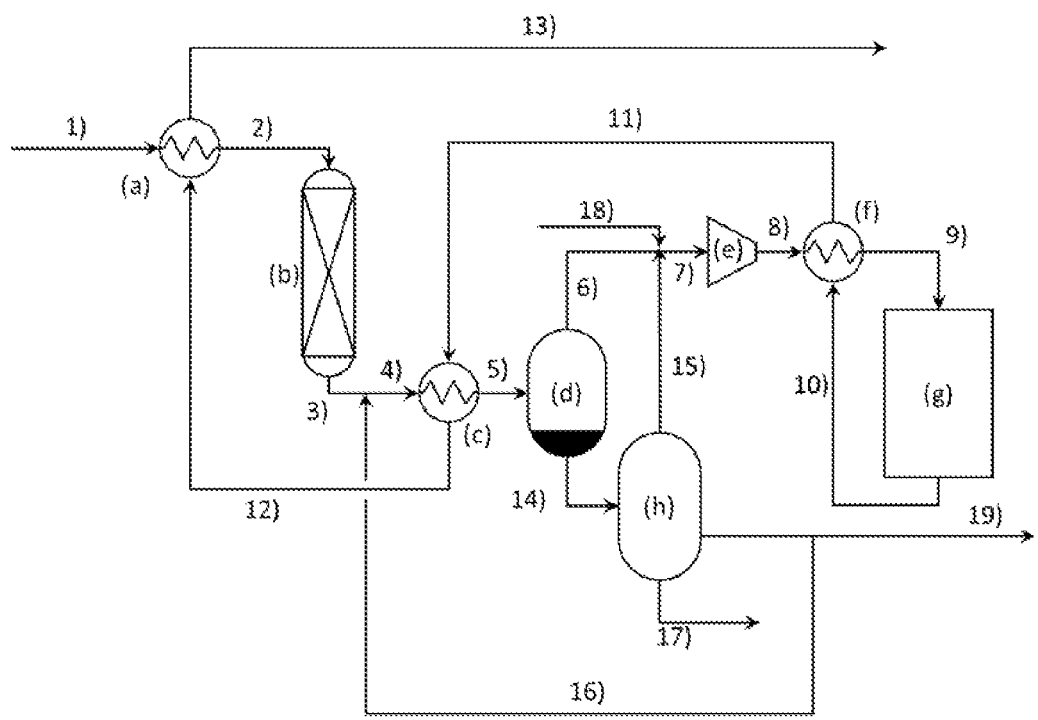

METHOD FOR TREATING AN ALCOHOL FEEDSTOCK FOR THE PRODUCTION OF OLEFINS

FIELD OF THE INVENTION

The present invention relates to a process for treating an alcoholic feedstock, in particular originating from fermentation, which is intended to be transformed. In particular, the present invention relates to a process for pretreating an alcohol feedstock for the production of corresponding olefins, for example a process for pretreating an ethanol feedstock for the production of ethylene.

STATE OF THE ART

The dehydration of alcohols in the presence of catalysts to produce olefins has indeed already been described. For example, patent FR 2 978 145 describes, in particular, a process for producing ethylene from an ethanol feedstock, in the presence of a dehydration catalyst.

Depending on the origin of the alcohols used, impurities may be present in the alcoholic feedstocks, the nature of these impurities and the content thereof being highly variable. Some of these impurities may be detrimental to the catalysts for the transformation reactions of the alcoholic feedstocks. Specifically, they can cause premature and/or significant deactivation of the dehydration catalysts. Some prior art studies describe pretreatments of the alcoholic feedstock prior to the catalytic dehydration.

In particular, in patent FR 2 978 145, the ethanol feedstock may undergo a stage of pretreatment in order to remove possible impurities contained in the feedstock, in particular nitrogen-comprising compounds and sulfur-comprising compounds, so as to limit the deactivation of the dehydration catalyst. This pretreatment stage uses, for example, means such as the use of resin(s), the adsorption of the impurities onto solids at a temperature between 20 and 60° C., a stage of hydrogenolysis followed by a stage of capture at a temperature of between 20 and 80° C. on an acidic solid and/or distillation. Patent FR 2 978 145 teaches that the oxygen-based compounds present in the feedstock are not removed and is silent as regards heavy impurities.

Patents FR 2 998 567 and FR 2 998 568 describe processes for dehydrating an ethanol feedstock to give ethylene, each comprising a stage of pretreatment of the ethanol feedstock on an acidic solid at a temperature of between 100 and 130° C. This pretreatment stage makes it possible to reduce the content of organic or basic nitrogen contained in the ethanol feedstock so as to limit the deactivation of the dehydration catalyst placed downstream. However, the patents FR 2 998 567 and FR 2 998 568 remain silent as regards the removal of heavy impurities possibly present in the feedstock or formed during the pretreatment on an acidic solid.

Patent application WO 2010/060981 discloses the pretreatment on an adsorbent of an—optionally biobased—ethanol feedstock, before the passage thereof into a reactor containing an acid catalyst, for example a dehydration catalyst to produce ethylene. The purpose of the pretreatment described in this application is to limit the inhibition or poisoning of the acid catalyst by components contained in the ethanol feedstock. The ethanol feedstock may optionally pass over a hydrogenation catalyst prior to passing over the adsorbent in order to convert at least a portion of the components which are harmful to the dehydration catalyst. Patent application WO 2010/060981 does not describe the possibility of using an acidic solid material, in particular a resin, or of increasing the molecular weight of harmful impurities.

Patent application JP H11043452 describes a treatment of an alcohol feedstock using an ion exchange resin, a kaolin clay or a zeolite to reduce the amount of basic nitrogen compounds to below 10 ppm by weight. However, it does not mention the removal of heavy impurities possibly present in the feedstock or formed during the treatment on resin, clay or zeolite.

Application WO 2014/127436 describes a process for the production of olefins by dehydration of ethanol comprising a stage of purification of the feedstock before evaporation and dehydration. The process described makes it possible to remove inorganic salts, such as potassium, sodium, calcium, iron, copper, sulfide, phosphorus and chloride salts, and organic compounds, such as organic acids, aldehydes, acetals, esters and hydrocarbons, which are compounds which are harmful to the dehydration catalysts. The purification stage of this process comprises the passage of the ethanol feedstock over a porous membrane, an adsorbent and/or an ion exchange resin, preferably the passage over a cation exchange resin and an anion exchange resin. However, application WO 2014/127436 does not address, inter alia, the problem of nitrogen-comprising impurities.

The present invention aims to improve, with respect to the prior art, the pretreatment of alcoholic feedstocks intended in particular for the production of olefins in order to increase the lifetime of the dehydration catalyst. It aims in particular to further reduce the content in the alcoholic feedstocks of impurities which are harmful to the dehydration catalyst and/or of impurities that risk accelerating the deactivation of the catalyst. More particularly, the present invention aims to propose an optimized process for treating an alcoholic feedstock in order, inter alia, to further limit the amount of nitrogen-comprising and/or sulfur-comprising compounds of any kind, i.e. organic or inorganic, basic or non-basic, light or heavy, without a loss of alcohol or of derivatives thereof.

OBJECT AND ADVANTAGE OF THE INVENTION

The invention relates to a process for treating an alcoholic feedstock containing at least one monoalcohol, comprising the following stages:
  a) a stage of preheating of said alcoholic feedstock to a temperature of between 70° C. and 200° C., to produce a preheated alcoholic feedstock;
  b) a stage of pretreatment of said preheated alcoholic feedstock on an acidic solid, operating at a temperature of between 70° C. and 200° C., to produce a pretreated alcoholic feedstock;
  c) a stage of partial vaporization of a vaporization feedstock to produce a gaseous stream and a liquid stream, said vaporization feedstock comprising said pretreated alcoholic feedstock obtained at the end of stage b), said partial vaporization stage comprising a partial vaporization section fed with said vaporization feedstock at an inlet pressure of between 0.1 and 1.4 MPa, to produce said gaseous stream and said liquid stream such that the gaseous stream represents at least 70% by weight of the weight of the vaporization feedstock;
  d) a stage of purification of the liquid stream resulting from stage c), to give a stream rich in water, a stream rich in monoalcohol and a stream rich in impurities.

Advantageously, said treatment process is integrated into a process for dehydrating said alcoholic feedstock and is placed upstream of the dehydration reactor(s). Said treatment process can, for example, be integrated upstream of the dehydration processes described in patents FR 2 978 145, FR 3 013 707, FR 3 013 708 and FR 3 026 406.

It has thus surprisingly been discovered that the treatment process according to the invention, comprising the sequence of a stage of pretreatment of an alcoholic feedstock on an acidic solid at a particular temperature followed by a stage of partial vaporization under the specific conditions of the invention, the latter stage preferably being coupled with an optional system for recycling the liquid streams, makes it possible to produce a purified alcoholic stream with limited losses of alcohol or derivatives thereof (for example the ethers derived from the target alcohol). The treatment process according to the invention specifically makes it possible to obtain a purified alcoholic stream with greatly reduced contents of nitrogen-comprising and/or sulfur-comprising compounds of any kind, in particular a content of elemental nitrogen originating from the nitrogen-comprising compounds of less than or equal to 3 ppm by weight, preferably less than or equal to 1 ppm by weight and even more preferably less than or equal to 0.5 ppm by weight relative to the total weight of the purified alcoholic stream, and a content of elemental sulfur, provided by the sulfur-comprising compounds, of less than or equal to 10 ppm by weight relative to the total weight of the purified alcoholic stream. Very preferably, the purified alcoholic stream obtained is devoid of these nitrogen-comprising and sulfur-comprising compounds which are "inhibitors" of the downstream dehydration catalyst. The treatment according to the invention also makes it possible to limit the content in the purified alcoholic stream of hydrocarbon-based impurities, in particular of carboxylic acid, which may cause premature and/or more or less significant coking of the dehydration catalyst. Thus, the lifetime of the catalyst used for the dehydration reaction is extended.

Another advantage of the present invention is the obtaining of a purified alcoholic effluent while at the same time limiting the consumption of utilities, in particular the energy consumption, compared to a treatment by distillation for example.

Advantageously, the process for treating said alcoholic feedstock is integrated into a more general process for dehydrating alcohol present in said alcoholic feedstock to give the corresponding olefin, downstream of the reaction stage. In this more general configuration and when the alcoholic feedstock is an ethanol feedstock intended to produce ethylene, another advantage of the treatment process according to the invention is the partial conversion of the ethanol into diethyl ether during the treatment of the ethanol feedstock, which contributes in particular to a limitation of the energy consumption of the overall process.

DETAILED DESCRIPTION OF THE INVENTION

According to the present invention, the expressions "alcoholic feedstock" and "alcohol feedstock", and variations thereof (for example "ethanol feedstock", "propanol feedstock" or "isobutanol feedstock"), are interchangeable and are used to characterize feedstocks comprising at least 35% by weight of a monoalcohol, preferably from 35% by weight to 99.9% by weight of monoalcohol. For example, the ethanol feedstock according to the invention comprises at least 35% by weight, preferably from 35% to 99.9% by weight of ethanol.

According to the invention, the term "monoalcohol" denotes an alcohol comprising a single hydroxyl group, preferably borne by a primary or secondary carbon, and a hydrocarbon chain comprising between 2 and 10 carbon atoms, preferably between 2 and 5 carbon atoms, which is linear or substituted, preferably in position 2, by an alkyl group. The term alkyl denotes a hydrocarbon compound of general formula $C_nH_{2n+1}$, where n is an integer between 1 and 20, preferably between 1 and 10, with preference between 1 and 5. Said monoalcohol is preferably ethanol, n-propanol, isopropanol, n-butanol, sec-butanol, isobutanol, 2-methyl-1-butanol or mixtures thereof. Very preferably, said monoalcohol is ethanol, n-propanol, isopropanol, isobutanol or mixtures thereof.

According to the present invention, the expression "between . . . and . . . " means that the limiting values of the interval are included in the range of values which is described. If such were not the case and if the limiting values were not included in the range described, such a clarification will be given by the present invention.

The invention relates to a process for treating (or purifying) an alcoholic feedstock containing at least one monoalcohol, said feedstock being in particular intended for the production of olefins, said treatment process comprising, preferably consisting of, the following stages:

a) a stage of preheating of said alcoholic feedstock to a temperature of between 70° C. and 200° C., preferably at a pressure of 0.1 to 3 MPa, to produce a preheated alcoholic feedstock;

b) a stage of pretreatment of said preheated alcoholic feedstock on an acidic solid, preferably an acidic resin, operating at a temperature of between 70° C. and 200° C., to produce a pretreated alcoholic feedstock;

c) a stage of partial vaporization of a vaporization feedstock to produce a gaseous stream and a liquid stream, said vaporization feedstock comprising said pretreated alcoholic feedstock obtained at the end of stage b), optionally as a mixture with a stream of external water and/or at least a portion of the stream of treated water recycled according to stage d), said streams of water optionally mixed with said pretreated alcoholic feedstock preferably being in the liquid state, said vaporization feedstock preferably having a water content of between 10% and 75% by weight relative to the vaporization feedstock, said partial vaporization stage comprising a partial vaporization section fed with said vaporization feedstock at an inlet pressure of between 0.1 and 1.4 MPa, preferably between 0.2 and 0.6 MPa, preferably at an inlet temperature of between 110° C. and 250° C., to produce said gaseous stream and said liquid stream such that the gaseous stream represents at least 70% by weight, preferably 80% by weight, preferentially 90% by weight, of the weight of the vaporization feedstock;

d) a stage of purification of the liquid stream resulting from stage c), preferably by distillation, in particular by stripping, to give a stream rich in water, a stream rich in monoalcohol and a stream rich in impurities, optionally followed by recycling of at least a portion of the stream rich in water to stage c) of mixing to produce said vaporization feedstock and/or by recycling of at least a portion of the stream rich in monoalcohol to the outlet of partial vaporization stage c) where it is mixed with said gaseous stream obtained at the end of stage c).

Advantageously, said treatment process is integrated into a process for dehydrating said alcoholic feedstock and is placed upstream of the dehydration reactor(s) to produce an olefin. Said treatment process can, for example, be integrated upstream of the dehydration processes described in patents FR 2 978 145, FR 3 013 707, FR 3 013 708 and FR 3 026 406.

The Feedstock

In accordance with the invention, the feedstock treated in the process according to the invention is an alcoholic feedstock (or an alcohol feedstock), containing at least one monoalcohol. Said monoalcohol is preferably ethanol, n-propanol, isopropanol, n-butanol, sec-butanol, isobutanol, 2-methyl-1-butanol or mixtures thereof. Very preferably, said monoalcohol is ethanol, n-propanol, isopropanol, isobutanol or mixtures thereof.

Advantageously, said alcohol feedstock of the process according to the invention comprises at least 35% by weight of said monoalcohol, preferably from 35% by weight to 99.9% by weight of said monoalcohol. Said alcoholic feedstock may also comprise between 0 and 65% water. Said alcoholic feedstock may also comprise impurities of mineral type (such as Na, Ca, P, Al, Si, K, $SO_4$), of organic type, such as methanol, ethanol, n-butanol, aldehydes, ketones and the corresponding acids, for example furanic, acetic or isobutyric acid. Said alcoholic feedstock also comprises, in particular, nitrogen-comprising and/or sulfur-comprising compounds of inorganic type, such as for example ammonia, or organic, preferably basic, nitrogen-comprising and/or sulfur-comprising compounds, such as amines, amides, imines and sulfur-comprising compounds (thiols, thiophenes, mercaptans, thioethers, sulfides, disulfides, etc.). The content of nitrogen and the content of sulfur, organic and inorganic, in said alcoholic feedstock are preferably each less than or equal to 0.5% by weight, preferably less than or equal to 0.2% by weight, the percentages by weight being expressed relative to the total weight of said alcoholic feedstock. According to the invention, the content of nitrogen and the content of sulfur should be understood to be the contents of elemental nitrogen and of elemental sulfur respectively provided by the nitrogen-comprising and sulfur-comprising impurities present in the streams under consideration, particularly in said feedstock of the process of the invention. Preferably, the content of elemental nitrogen is advantageously determined by combustion and detection by chemiluminescence and the content of elemental sulfur is determined by combustion and detection by UV fluorescence, according to the invention.

Advantageously, said alcoholic feedstock may originate from non-fossil resources. Preferably, the alcoholic feedstock treated in the process according to the invention is produced from renewable resources derived from biomass, preferably by fermentation of sugars obtained, for example, from sugar-yielding plant crops such as sugarcane (saccharose, glucose, fructose and sucrose), from beets, or from starchy plants (starch) or from lignocellulosic biomass or from hydrolyzed cellulose (predominantly glucose, and xylose and galactose), containing variable amounts of water. For a more complete description of the conventional fermentation processes, reference may be made to the publication "Les Biocarburants, État des lieux, perspectives et enjeux du développement [Biofuels, current state, perspectives and development challenges]", Daniel Ballerini, published by Technip.

Said alcoholic feedstock may also advantageously be obtained from synthesis gas.

The alcoholic feedstock treated in the process according to the invention may also optionally be obtained via an alcohol synthesis process proceeding from fossil resources, for instance proceeding from coal, natural gas or carbon-based waste.

Said alcoholic feedstock of the process according to the invention may also advantageously also be obtained from hydrogenation of the corresponding acids or esters. In this case, acetic acid or acetic esters are advantageously hydrogenated using hydrogen to give ethanol. Acetic acid may advantageously be obtained by carbonylation of methanol or by fermentation of carbohydrates.

Preferably, the alcoholic feedstock treated in the process according to the invention is an alcohol feedstock produced from renewable resources derived from biomass.

Preheating Stage a)

According to the invention, the alcohol feedstock undergoes a stage a) of preheating to a temperature of between 70° C. and 200° C., to produce a preheated alcoholic feedstock.

According to the invention, the expression "preheating to a temperature of between 70° C. and 200° C." means that, at the end of stage a), the alcohol feedstock is at a temperature of between 70° C. and 200° C. Preferably, preheating stage a) is operated at a temperature of between 100° C. and 180° C., preferentially between 110° C. and 160° C.

Advantageously, the pressure of the alcohol feedstock is adjusted such that said feedstock remains liquid at the end of preheating stage a). Preferably, the pressure of said preheated alcoholic feedstock is between 0.1 and 3 MPa.

The alcoholic feedstock is advantageously preheated in a heat exchanger, by means of an exchange of heat with a heat source external to the process according to the invention, for example by direct heating (for example in an oven) or any other technique known to those skilled in the art.

When the treatment process according to the invention is integrated into a more general process for dehydrating said alcoholic feedstock to produce an olefin, the alcoholic feedstock is advantageously preheated in a heat exchanger by means of an exchange of heat with the dehydration effluent resulting from the final dehydration reactor.

Pretreatment Stage b)

According to the invention, the preheated alcoholic feedstock, resulting from preheating stage a), undergoes a pretreatment stage b) so as to produce a pretreated alcoholic feedstock.

Advantageously, said pretreatment stage b) is operated at a temperature of between 70° C. and 200° C., preferably between 100° C. and 180° C., preferentially between 110° C. and 160° C., and preferably at a pressure of between 0.1 and 3 MPa. Under these operating conditions, the alcoholic feedstock advantageously remains in liquid form.

Said pretreatment stage b) is performed on an acidic solid. Said acidic solid can be chosen from all the solids known to those skilled in the art. Said acidic solid may thus be selected from the group consisting of: acidic clays, zeolites, sulfated zirconias, acidic resins, etc. The most important thing is that the acidic solid possesses a high exchange capacity for capturing a maximum of the basic and cationic species.

When the alcoholic feedstock is an ethanol feedstock, the acidic solid should also advantageously possess a sufficiently high acid strength to bring about the partial transformation of ethanol into DEE.

For example, said acidic solid can be chosen from commercially available acidic solids, such as clays treated with acids to make them acidic (such as montmorillonite) and zeolites preferably having a molar silica-to-alumina ratio in the crystal lattice of 2.5 to 100.

Preferably, said acidic solid is an acidic resin, especially an ion exchange resin, preferably cation exchange resin, in particular possessing an exchange capacity (or acid strength) of at least 0.1 mmol H$^+$ equivalent per gram, the exchange capacity (or acid strength) being determined by assay, preferably by conductimetry, of the H+ ions released by the acidic resin after exchange with Na+ ions (cf. in particular ASTM D4266). More particularly, said acidic resin comprises sulfonic groups grafted to an organic support composed of aromatic and/or haloaliphatic chains. Said acidic resin is typically prepared by polymerization or copolymerization of vinylaromatic groups followed by sulfonation, said vinylaromatic groups being chosen from styrene, vinyltoluene, vinylnaphthalene, vinylethylbenzene, methylstyrene, vinylchlorobenzene, and vinylxylene. Said acidic resin advantageously has a degree of crosslinking of between 20% and 35%, preferably between 25% and 35% and with preference equal to 30%, and an acid strength (or exchange capacity), determined by assay, preferably by conductimetry, of the H+ ions released by the acidic resin after exchange with Na+ ions (cf. ASTM D4266), of from 0.2 to 10 mmol H$^+$ equivalent per gram, preferably between 0.2 and 6 mmol H$^+$ equivalent per gram. A preferred resin is a copolymer of monovinylaromatics and polyvinylaromatics, preferably a copolymer of divinylbenzene and of styrene, in particular having a degree of crosslinking of between 20% and 45%, preferably between 30% and 40%, and with preference equal to 35%, and an acid strength, representing the number of active sites in said resin, determined by assay, preferably by conductimetry, of the H+ ions released by the acidic resin after exchange with Na+ ions (cf. ASTM D4266), of between 1 and 10 mmol H$^+$ equivalent per gram, and preferably of between 3.5 and 6 mmol H$^+$ equivalent per gram. For example, the acidic solid is a commercial acidic resin sold under the reference TA801 by Axens.

Preferably, said acidic resin is in the form of particles with a size of between 0.15 and 1.5 mm. The term "size of the resin particles" is understood to mean the mean equivalent diameter of said particles. The term "equivalent diameter" of a particle is understood to mean the diameter equivalent to a sphere behaving identically during the chosen particle size analysis operation. The size of the particles of said acidic resin is measured by any technique known to those skilled in the art, preferably by screening on a column of suitable screens according to a technique known to those skilled in the art.

The acidic solid can be regenerated from time to time, in particular once its exchange capacity becomes limited, a sign that its active sites are almost saturated by the adsorption of the basic and/or cationic species in situ or ex situ. In the case of inorganic acidic solids such as acidic clays and zeolites, regeneration can consist of simple heating at high temperature in order to desorb the basic species in the presence of an inert or oxygen-containing stream. Cations can be removed by ion exchange. In the case of acidic resins, the latter can be regenerated by ion exchange, typically by treatment with an acid in the liquid phase. The acidic solid can also be used once, until saturation, and replaced with virgin acidic solid.

Said acidic solid of said stage b) can be used alone or as a mixture with other types of acidic solids. Mixtures of different acidic solids or sequences of acidic solids may be used in order to optimize in particular the capacity for adsorption of the basic and/or cationic species and possibly, in the case of an ethanol feedstock, the capacity to partially transform the ethanol into DEE.

The pretreatment described above can advantageously be supplemented by a pretreatment using an anion exchange resin. This resin can for example be a resin loaded with sodium, or trimethylammonium characterized by an exchange capacity measured in mg(OH$^-$)/liter. This resin can for example be Amberlite IRN78 resin. This additional resin advantageously makes it possible to retain inorganic anions, for example sulfate $SO_4^{2-}$ ions, and therefore can contribute to extending the life of the dehydration catalyst.

Advantageously, said pretreatment stage b) makes it possible to trap and therefore remove cationic and possibly anionic impurities, basic, complexing, chelating impurities, inorganic or organic impurities, in particular metal salts (such as K, Na, Ca, Fe, Cu, P, Cl salts) and nitrogen-comprising and/or sulfur-comprising impurities, such as basic nitrogen compounds present in the feedstock, for example in the form of ammonia and/or in the form of organic and basic species, for example in amine, amide, imine or nitrile form.

Said pretreatment stage b) also induces the transformation of certain, in particular organic, nitrogen-comprising and/or sulfur-comprising species into heavier nitrogen-comprising and/or sulfur-comprising compounds. These heavy compounds are for example sediments, inorganic salts, organic salts, sulfur-comprising compounds and other heavy impurities, and the like. These heavy compounds are not trapped by said acidic solid and by the optionally used anion exchange resin during said pretreatment stage b) and can be found in said pretreated alcoholic feedstock produced at the end of said stage b) of the process according to the invention.

Partial Vaporization Stage c)

According to the invention, the treatment process according to the invention comprises a stage of partial vaporization of a vaporization feedstock, comprising said pretreated alcoholic feedstock resulting from stage b), so as to produce a gaseous stream and a liquid stream. Said gaseous stream produced at the end of stage c) of the process of the invention advantageously comprises at least said monoalcohol.

According to the invention, the expression "vaporization feedstock" corresponds to a feedstock comprising at least the pretreated alcoholic feedstock resulting from stage b). Said vaporization feedstock may also advantageously comprise a recycled stream of water purified according to stage d) and/or a stream of water external to the process according to the invention. Preferably, the water content of the vaporization feedstock is preferentially between 10% and 75% by weight of water relative to the total weight of the vaporization feedstock. With such a water content, the partial pressures of the alcohol will be lowered in the dehydration reactor(s), making it possible to render the process more selective for the targeted olefin.

According to the invention, said partial vaporization stage c) comprises a partial vaporization section, advantageously comprising a heat exchanger for heating said vaporization feedstock and a flash evaporator (or vaporization vessel) for enabling the gas/liquid separation of the vaporization feedstock heated and partially vaporized in the heating system. Said partial vaporization section is fed with said vaporization feedstock at an inlet pressure of between 0.1 and 1.4 MPa, preferably between 0.2 and 0.6 MPa. Preferably, the temperature of said vaporization feedstock is adjusted in said partial vaporization section to a temperature of between 110° C. and 250° C.

Advantageously, the heat exchanger of said partial vaporization section in stage c), placed upstream of the flash evaporator (or vaporization vessel), makes it possible to adjust the temperature of said vaporization feedstock to obtain the desired vaporized amount, that is to say the desired amount of gaseous stream at the end of stage c). Preferably, the heat exchanger of said partial vaporization section makes it possible to adjust the temperature of said vaporization feedstock to a temperature of between 110° C. and 250° C. The heat exchanger advantageously makes it possible to adjust the temperature of said vaporization feedstock, by means of an exchange of heat with a heat source external to the process according to the invention, for example by direct heating (for example in an oven) or any other technique known to those skilled in the art. When the treatment process according to the invention is integrated into a more general process for producing olefins by dehydration of said alcohol feedstock, the vaporization feedstock is advantageously heated, during partial vaporization stage c), in a heat exchanger by means of an exchange of heat with the dehydration effluent resulting from the final dehydration reactor.

Said partial vaporization stage c) of the process according to the invention produces a gaseous stream (or vaporized stream) at the top of the flash evaporator of said partial vaporization section and a liquid stream at the bottom of said flash evaporator. Advantageously, the gaseous stream recovered at the top of the vaporization vessel of said partial vaporization section represents at least 70% by weight, preferably 80% by weight, preferentially 90% by weight, of the weight of the vaporization feedstock which is introduced into the vaporization vessel. Preferably, said gaseous stream represents a proportion of less than or equal to 98% by weight, preferentially less than or equal to 95% by weight, of the weight of the vaporization feedstock introduced into the vaporization vessel.

Said gaseous stream recovered at the top predominantly comprises said monoalcohol, i.e. at least 55% by weight of monoalcohol, preferably at least 60% by weight of monoalcohol, preferentially at least 70% by weight of monoalcohol and with preference at least 80% by weight of monoalcohol, relative to the total weight of the gaseous stream. The content of impurities in said gaseous stream recovered at the top of the partial vaporization section is low. Preferably, the content of elemental nitrogen in said gaseous stream, the nitrogen being provided by the nitrogen-comprising impurities, i.e. the organic and/or inorganic nitrogen-comprising compounds, is less than or equal to 3 ppm by weight, preferentially less than or equal to 1 ppm by weight and with preference less than or equal to 0.5 ppm by weight, relative to the total weight of said gaseous stream, the content of elemental nitrogen advantageously being determined by combustion and detection by chemiluminescence. At the same time, the content of elemental sulfur in said gaseous stream, provided by the sulfur-comprising impurities, i.e. the organic and/or inorganic sulfur-comprising compounds, is preferably less than or equal to 10 ppm by weight, preferentially less than or equal to 5 ppm by weight and with preference less than or equal to 1 ppm by weight, relative to the total weight of said gaseous stream, the content of elemental sulfur advantageously being determined by combustion and detection by UV fluorescence. Said gaseous stream (or vaporized stream) recovered at the top of the vaporization vessel may also comprise water. It may also comprise an intermediate of the dehydration reaction of said monoalcohol, for example diethyl ether (DEE) which is an intermediate of the dehydration reaction of ethanol, at contents of generally less than or equal to 20% by weight, preferably less than or equal to 15% by weight, and with preference less than or equal to 10% by weight, relative to at least total of said gaseous stream.

At the end of said partial vaporization stage c), and preferably before being used in later stages of an overall dehydration process, the gaseous stream (or vaporized stream) obtained, which predominantly comprises said monoalcohol, may optionally be mixed with a stream rich in said monoalcohol, resulting from stage d) of purification of the liquid stream. It may also optionally be mixed with a stream of external water and/or with a stream rich in water resulting from stage d) of the process according to the invention in order to adjust the water content to a content by weight of between 10% and 75% by weight of water relative to the total weight of the stream after mixing. At such water contents, the partial pressure of said monoalcohol is lowered in the dehydration reactor(s), placed downstream of the treatment process according to the invention, making it possible to render the overall dehydration process more selective for the targeted olefin.

Said liquid stream recovered at the bottom of the flash evaporator (or vaporization vessel) collects together the majority of the impurities present in the pretreated feedstock, and consequently of the alcoholic feedstock treated by the process according to the invention. Preferably, said liquid stream obtained at the end of stage c) of the process according to the invention contains at least 70% by weight, preferentially at least 80% by weight, and with preference at least 90% by weight, of the nitrogen and sulfur provided by the organic and/or inorganic, light and/or heavy, nitrogen-comprising and sulfur-comprising compounds present in the alcoholic feedstock feeding the process according to the invention. Said liquid stream recovered at the bottom of the partial vaporization section may also comprise water and/or said monoalcohol. Said liquid stream may also comprise traces of said intermediate of the dehydration reaction of the monoalcohol, for example traces of diethyl ether (DEE) which is an intermediate of the dehydration reaction of ethanol when the alcohol feedstock treated by the process according to the invention is an ethanol feedstock.

Stage d) of Purification of the Liquid Stream

In accordance with the invention, the treatment process according to the invention comprises a stage of purification of the liquid stream resulting from partial vaporization stage c), to produce a stream rich in water, a stream rich in monoalcohol and a stream rich in impurities.

Advantageously, said liquid stream resulting from stage c) of the process according to the invention is treated, during said stage d), in a section for purification, preferably by distillation, very preferably by stripping (i.e. distillation without reflux). Those skilled in the art will know how to adapt the operating conditions of the purification section, in particular of the stripping. For example, the pressure in the stripping column can be between 0.1 and 3 MPa and the temperature at the bottom of the stripping column varies, for example, between 80 and 250° C.

Said stream rich in said monoalcohol, preferably in gaseous form, is recovered at the top of the purification section. Advantageously, it comprises at least 70% by weight, preferably at least 80% by weight, with preference at least 90% by weight, of monoalcohol. Said stream rich in said monoalcohol is optionally at least partially recycled and mixed with the gaseous stream obtained at the end of stage c).

Said stream rich in impurities is recovered at the bottom of said purification section. Said stream rich in impurities comprises nitrogen-comprising and/or sulfur-comprising impurities. It can also comprise metal salts.

The water-rich stream (or stream of purified water) resulting from said purification section preferably comprises at least 70% by weight of water, with preference at least 80% by weight of water and more preferably still at least 90% by weight of water. Advantageously, at least a portion of said stream rich in water (or stream of purified water) resulting from the purification section is recycled to the inlet of stage c) and mixed with the pretreated alcoholic feedstock obtained at the end of pretreatment stage b) to produce the vaporization feedstock. Said stream of purified water may also advantageously be at least partially recycled to the outlet of stage c) of the process according to the invention and mixed with the gaseous stream obtained at the end of said partial vaporization stage c).

Optional Compression Stage e)

In one particular embodiment, in particular when said treatment process according to the invention is directly integrated into a more general dehydration process, said vaporized stream (or gaseous stream) resulting from stage c) of the process according to the invention, optionally mixed with at least a portion of the stream rich in alcohol recycled and resulting from stage d) and/or optionally mixed with a stream of external water and/or with at least a portion of said stream rich in water recycled and resulting from stage d), may undergo, upstream of the dehydration reactor(s), an optional stage of compression so as to produce a compressed feedstock. Said compression stage is advantageously performed in any type of compressor known to those skilled in the art. In particular, the compression stage is advantageously performed in a compressor of integrally geared radial type or in a compressor comprising one or more fans with a radial wheel placed in series without intermediate cooling or in a positive displacement-type compressor with or without lubrication.

In the case where optional compression stage e) is carried out, said vaporization feedstock is introduced into said vaporization stage c) at a pressure of between 0.1 and 1.4 MPa, preferentially of between 0.2 and 0.6 MPa. The pressure of said compressed feedstock at the end of optional compression stage e) is advantageously between 0.3 and 1.8 MPa, preferentially between 0.5 and 1.3 MPa.

Very advantageously, the process for treating the alcoholic feedstock according to the invention, optionally comprising said optional compression stage e), can be integrated into a more general dehydration process such as one of the processes described in patents FR 2 978 145, FR 3 013 707, FR 3 013 708 and FR 3 026 406.

Advantageously, the treatment process according to the invention makes it possible to remove the impurities present in an alcoholic feedstock, in particular organic and/or inorganic nitrogen-comprising and/or sulfur-comprising impurities, whether these be light or heavy. The process according to the invention, which comprises a sequence of specific stages, makes it possible in particular to remove the heavy impurities formed during the stage of pretreatment on an acidic solid and/or already present in the alcoholic feedstock. In particular, the content, in the alcoholic dehydration feedstock treated by the process according to the invention (the alcoholic dehydration feedstock treated by the process according to the invention corresponding to the alcoholic stream obtained after the treatment process according to the invention, that is to say corresponding to the gaseous stream resulting from stage c) of the process according to the invention optionally mixed with the recycled stream rich in monoalcohol resulting from stage d) and/or with a stream of external water or a recycled stream rich in water resulting from stage d) of the process according to the invention), of elemental nitrogen provided by the organic and/or inorganic nitrogen-comprising impurities is preferably less than or equal to 3 ppm by weight, preferentially less than or equal to 1 ppm by weight and with preference less than or equal to 0.5 ppm by weight, relative to the total weight of said treated alcoholic feedstock. The content, in the alcoholic dehydration feedstock treated by the process according to the invention, of elemental sulfur provided by the organic and/or inorganic sulfur-comprising impurities is preferably less than or equal to 10 ppm by weight, preferentially less than or equal to 5 ppm by weight and with preference less than or equal to 1 ppm by weight, relative to the total weight of said treated alcoholic feedstock.

Thus, the alcoholic stream obtained by the treatment process according to the invention has a greatly reduced content of impurities which accelerate the deactivation of the dehydration catalysts, or even is devoid of these impurities, very advantageously enabling a substantial extension of the lifetime of the dehydration catalysts used subsequently to the treatment process according to the invention.

Very advantageously, according to the invention, the content of elemental nitrogen provided by the nitrogen-comprising impurities present in the stream under consideration, in particular in the alcoholic stream obtained by the treatment process according to the invention, is determined by combustion and detection by chemiluminescence, and the content of elemental sulfur provided by the sulfur-comprising impurities is determined by detection by chemiluminescence and the content of elemental sulfur is determined by combustion and detection by UV fluorescence.

The treatment process according to the invention also makes it possible to advantageously envisage a broad range of alcoholic feedstocks for the production of olefins by dehydration.

The figures and examples that follow illustrate the invention without limiting the scope thereof.

DESCRIPTION OF THE FIGURES

FIG. 1 schematically shows an embodiment of the process for treatment according to the invention of the alcoholic feedstock of a dehydration section, in which at least a portion of the stream rich in water and the stream rich in monoalcohol which are produced are recycled and in which the vaporized stream and the recycled stream rich in monoalcohol are compressed.

The alcohol feedstock 1) is preheated in the exchanger (a), and then introduced into a pretreatment zone (b) via the pipe 2). The pretreated alcohol feedstock 3) is then mixed in the pipe 4) with a portion of the stream rich in water resulting from the purification zone (h) which is recycled via the pipe 16).

The pretreated alcohol feedstock mixed with the recycled portion of the stream rich in water is introduced into a gas/liquid exchanger (c). Said mixture undergoes an exchange of heat with the effluent coming from the reaction zone (g) which enters the exchanger via the pipe 11). The heated mixture is sent via the pipe 5) to a flash evaporator (d). Said heated mixture undergoes partial vaporization to produce a gaseous stream recovered via pipe 6) and a liquid stream recovered via pipe 14).

The liquid stream recovered at the bottom of the flash vessel is sent via pipe 14) to the purification zone (h) where it undergoes stripping to produce a purified stream rich in alcohol recovered via pipe 15), a purified stream of water recovered via pipes 16 and 19) and a stream rich in impurities recovered via pipe 17).

The gaseous stream 6) which consists of a stream rich in alcohol is mixed in pipe 7) with the recycled purified alcohol stream resulting from the purification zone (h) via pipe 15).

Optionally, the water content in pipe 7) can be adjusted with a stream of external water or coming from a purified stream of water, for example a portion of the stream of purified water resulting from the purification zone (h). The alcohol stream 7), possibly diluted, is sent to a compressor (e) via pipe 7).

At the outlet of the compressor (e), the compressed stream is then introduced via pipe 8) into an exchanger (f) in which it undergoes an exchange of heat with the effluent coming from the reaction zone (g), the latter then being cooled without condensation towards pipe 11). The preheated compressed stream is sent to the reaction section (g). The reaction effluent 10) leaving the reaction section (g) passes through the exchanger (f) where it is cooled without condensation towards pipe 11), then through a gas/liquid exchanger where it is partially condensed into a stream 12), and lastly through the exchanger (a) used to preheat the alcohol feedstock entering the pretreatment zone (b). The cooled reaction effluent 13) can then be sent to a purification section.

EXAMPLES

In the following examples, the ethanol and diethyl ether (DEE) contents are determined by gas chromatography. The water content is determined by the Karl Fischer method. The nitrogen and sulfur contents are contents of elemental nitrogen and of elemental sulfur, respectively provided by the nitrogen-comprising and sulfur-comprising impurities present in the analyzed streams. The elemental nitrogen content is determined by combustion and detection by chemiluminescence. The elemental sulfur content is determined by combustion and detection by UV fluorescence.

Example 1: In Accordance with the Invention

Example 1 illustrates the advantage of a process according to the invention comprising a sequence of stages of pretreatment and of partial vaporization of the ethanol feedstock, upstream of a dehydration unit.

The ethanol feedstock under consideration is produced by the fermentation of wheat, without extraction of gluten, by a process of dry milling type.
Stages a) and b)

The ethanol feedstock is preheated to 130° C., and then is pretreated on a TA801 resin (supplied by Axens). During this pretreatment, the hourly space velocity (HSV) of the total ethanol feedstock relative to the volume of resin is 1 h$^{-1}$, the temperature is 130° C. and the pressure is maintained at 0.5 MPa. The characteristics of the crude and pretreated ethanol feedstock are given in table 1.

TABLE 1

Characteristics of the ethanol feedstock before and after pretreatment on the TA 801 resin

|  | CRUDE ETHANOL FEEDSTOCK | PRETREATED ETHANOL FEEDSTOCK |
|---|---|---|
| ETHANOL (% by weight) | 90.3% | 80.2% |
| H$_2$O (% by weight) | 9.5% | 11.4% |
| DEE (% by weight) | not detected | 8.2% |
| NITROGEN* (ppm by weight) | 5.2 ppm | 2.5 ppm |
| SULFUR** (ppm by weight) | 3 ppm | 14 ppm |

*content of elemental nitrogen provided by the nitrogen-comprising compounds present in the feedstock before and after pretreatment
**content of elemental sulfur provided by the sulfur-comprising compounds present in the feedstock before and after pretreatment It appears that the contents of nitrogen-comprising and sulfur-comprising compounds in the ethanol feedstock pretreated on the acidic resin remain significant (2.5 ppm by weight of nitrogen and 14 ppm by weight of sulfur).

In addition, during this pretreatment, a portion of the ethanol is converted into diethyl ether (DEE).
Stage c)

The pretreated feedstock is then partially vaporized. The pressure of the pretreated ethanol feedstock at the inlet of the partial vaporization section is 0.45 MPa.

A gaseous stream corresponding to 90.5% by weight of the weight of the pretreated ethanol feedstock introduced into the flash vessel is recovered at the top of the flash vessel and 9.5% by weight of the weight of the vaporization feedstock is recovered in liquid form at the bottom of the flash vessel. The characteristics of the vaporized ethanol feedstock (gaseous stream) and of the liquid stream which are recovered are presented in table 2.

TABLE 2

Characteristics of the pretreated ethanol feedstock and of the gaseous (vaporized feedstock) and liquid (liquid stream) streams after partial vaporization

|  | PRETREATED ETHANOL FEEDSTOCK | VAPORIZED ETHANOL FEEDSTOCK | LIQUID STREAM |
|---|---|---|---|
| ETHANOL (% by weight) | 80.2% | 82.2% | 61.1% |
| H$_2$O (% by weight) | 11.4% | 9.1% | 33.3% |
| DEE (% by weight) | 8.2% | 8.7% | 3.4% |
| NITROGEN* (ppm by weight) | 2.5 ppm | 0.5 ppm | 21.6 ppm |
| SULFUR** (ppm by weight) | 14 ppm | 1.5 ppm | 133.1 ppm |

*content of elemental nitrogen provided by the nitrogen-comprising compounds present
**content of elemental sulfur provided by the sulfur-comprising compounds present It is clearly apparent that the majority of the nitrogen-comprising and sulfur-comprising impurities in the pretreated ethanol feedstock are found in the liquid stream recovered at the bottom of the flash vessel:
  approximately 82% by weight (i.e. (9.5%×21.6)/2.5) of the nitrogen of the pretreated feedstock is found in the liquid stream and only approximately 18% by weight (i.e. (90.5%×0.5)/2.5) of the nitrogen from the pretreated feedstock is found in the gaseous stream recovered at the top;
  approximately 90% by weight (i.e. (9.5%×133.1)/14) of the sulfur of the pretreated feedstock is found in the liquid stream and only approximately 10% by weight (i.e. (90.5%×1.5)/14) of the sulfur from the pretreated feedstock is found in the gaseous stream recovered at the top.

The nitrogen and sulfur contents of the vaporized ethanol feedstock recovered after the sequence of the pretreatment on resin and then the partial vaporization are low: the nitrogen content of the vaporized ethanol feedstock is 0.5 ppm by weight and the sulfur content of the vaporized ethanol feedstock is 1.5 ppm by weight, relative to the total weight of said vaporized ethanol stream.

Purification Stage d)

The liquid stream is sent to a stripper (or a distillation column without reflux) to produce an ethanol stream recovered at the top of the column, a water stream and a residue, recovered at the bottom of the column.

Use of the Gaseous Stream: Dehydration Stage

The vaporized feedstock is sent to the dehydration section. The dehydration reaction is carried out in a pilot-sized fixed-bed reactor. The catalyst used is that used for the dehydration of ethanol as described in patent WO 2013/011208. This comprises 80% by weight of ZSM-5 zeolite treated with $H_3PO_4$ so that the phosphorus P content is 3% by weight. For the purposes of the test, the catalyst was ground beforehand.

The operating conditions are as follows: HSVtotal=21 $h^{-1}$ (HSV for hourly space velocity, defined as the ratio of the hourly volume flow rate of the introduced feedstock to the volume of catalyst), P=0.2 MPa. The temperature of the reaction is adjusted in order to achieve a conversion of greater than 99.9% of the ethanol in the feedstock used.

The test starts with a mixture of 90% by weight of pure ethanol and 10% by weight of pure water, in order to create a reference. After 48 hours of stabilization, the vaporized feedstock recovered previously is injected, and then the crude ethanol feedstock is injected in turn.

Table 3 shows the temperatures necessary to achieve the 99.9% conversion of the ethanol in the feedstock introduced into the reactor.

TABLE 3

Reaction temperatures in the presence of pure ethanol + 10% by weight of water, of the vaporized feedstock and of the crude ethanol feedstock (HSV = 21 $h^{-1}$, P = 0.2 MPa)

| | PURE ETHANOL + 10 wt % of WATER | VAPORIZED ETHANOL FEEDSTOCK | CRUDE ETHANOL FEEDSTOCK |
|---|---|---|---|
| Temperature (° C.) | 400° C. | 400° C. | 455° C. |

It appears that, in the presence of the vaporized feedstock recovered at the end of the treatment according to the invention, the temperature for achieving a conversion of 99.9% is not changed compared to a reference pure ethanol feedstock. In contrast, when the ethanol introduced is the crude ethanol feedstock, comprising impurities, in particular nitrogen-comprising and sulfur-comprising impurities, it is necessary to increase the temperature by 55° C. to maintain a conversion of 99.9%. Thus, the lifetime of the dehydration catalyst will be extended when the ethanol feedstock is treated by the process according to the invention, compared to the crude ethanol feedstock.

Example 2: Not in Accordance with the Invention

Example 2 illustrates the effect on the dehydration reaction of a process for treating the ethanol feedstock comprising only the partial vaporization stage (not in accordance with the invention).

In this example, the ethanol feedstock under consideration is the same as that of example 1: it is produced by the fermentation of wheat, without extraction of gluten, by a process of dry milling type.

The ethanol feedstock is sent to a partial vaporization section, at an inlet pressure of 0.45 MPa. The temperature is adjusted so as to produce a gaseous stream corresponding to 89.4% by weight of the weight of the ethanol feedstock and a liquid stream corresponding to 10.6% by weight of the weight of the ethanol feedstock recovered at the bottom of the flash vessel. The characteristics of the gaseous stream and of the liquid stream which are recovered are presented in table 4.

TABLE 4

Characteristics of the crude ethanol feedstock and of the gaseous and liquid streams obtained after partial vaporization

| | CRUDE ETHANOL FEEDSTOCK | GASEOUS STREAM | LIQUID STREAM |
|---|---|---|---|
| ETHANOL (% by weight) | 90.3% | 92.9% | 68.4% |
| $H_2O$ (% by weight) | 9.5% | 7.1% | 29.7% |
| DEE (% by weight) | not detected % | not detected | not detected |
| NITROGEN* (ppm by weight) | 5.2 ppm | 4.2 ppm | 13.6 ppm |
| SULFUR** (ppm by weight) | 3 ppm | 2.2 ppm | 10.7 ppm |

*content of elemental nitrogen provided by the nitrogen-comprising compounds present
**content of elemental sulfur provided by the sulfur-comprising compounds present The nitrogen and sulfur contents in the gaseous stream recovered after partial vaporization remain relatively high: the content of elemental nitrogen is 4.2 ppm by weight and the sulfur content is 13.6 ppm by weight relative to the total weight of the gaseous stream.

As described in example 1, the gaseous stream obtained is sent to a dehydration section and is tested under similar conditions:

The dehydration reaction is carried out in a pilot-sized fixed-bed reactor. The catalyst used comprises 80% by weight of ZSM-5 zeolite treated with $H_3PO_4$ so that the phosphorus P content is 3% by weight. The catalyst was ground prior to the test.

The operating conditions are as follows: HSVtotal=21 $h^{-1}$ (HSV for hourly space velocity, defined as the ratio of the hourly volume flow rate of the introduced feedstock to the volume of catalyst), P=0.2 MPa. The temperature of the reaction is adjusted in order to achieve a conversion of greater than 99.9% of the ethanol in the feedstock used.

The test starts with a mixture of 90% by weight of pure ethanol and 10% by weight of pure water, in order to create a reference. After 48 hours of stabilization, the gaseous stream recovered previously is injected, and then the crude ethanol feedstock is injected in turn.

Table 5 shows the temperatures necessary to achieve the 99.9% conversion of the ethanol in the feedstock introduced into the reactor.

TABLE 5

Reaction temperatures in the presence of pure ethanol +
10% by weight of water, of the gaseous stream obtained
and of the crude ethanol feedstock (HSV = 21 h$^{-1}$, P = 0.2 MPa)

|  | PURE ETHANOL +<br>10 wt % of WATER | GASEOUS<br>STREAM | CRUDE<br>ETHANOL<br>FEEDSTOCK |
|---|---|---|---|
| Temperature (° C.) | 400° C. | 449° C. | 455° C. |

In the presence of the gaseous stream recovered at the outlet of the partial vaporization section, described in example 2 (not in accordance), that is to say after treatment of the ethanol feedstock comprising only partial vaporization (no pretreatment on acidic solid), the dehydration temperature to achieve 99.9% conversion is greatly increased (+49° C.) compared to the reference test (pure ethanol with 10% water) and compared to the vaporized ethanol feedstock recovered as described in example 1 (in accordance), that is to say after treatment of the ethanol feedstock comprising a pretreatment on acidic resin and partial vaporization. This increase in reaction temperature is indicative of a premature deactivation of the dehydration catalyst.

Example 3: In Accordance with the Invention

Example 3 illustrates the advantage of a process according to the invention comprising a sequence of stages of pretreatment and of partial vaporization of the ethanol feedstock, upstream of a dehydration unit.

The ethanol feedstock under consideration is produced by the fermentation of wheat. This is the phlegm (or phlegm ethanol), i.e. the crude ethanol obtained after a simple distillation.

The ethanol feedstock is preheated to 135° C., and then is pretreated on a TA801 resin (from Axens). During this pretreatment, the HSV of the total ethanol feedstock over the resin is 1 h$^{-1}$, the temperature is 135° C. and the pressure is maintained at 0.5 MPa. The characteristics of the crude and pretreated ethanol feedstock are given in table 6.

TABLE 6

Characteristics of the ethanol feedstock before and after
pretreatment on the TA 801 resin

|  | PHLEGM<br>ETHANOL<br>FEEDSTOCK | PRETREATED<br>ETHANOL<br>FEEDSTOCK |
|---|---|---|
| ETHANOL (% by weight) | 89.8% | 78.9% |
| H$_2$O (% by weight) | 9.9% | 12.0% |
| DEE (% by weight) | not detected | 8.8% |
| NITROGEN* (ppm by weight) | 3.2 ppm | 0.6 ppm |
| SULFUR** (ppm by weight) | 63.6 ppm | 65.5 ppm |

*content of elemental nitrogen provided by the nitrogen-comprising compounds present in the feedstock before and after pretreatment
**content of elemental sulfur provided by the sulfur-comprising compounds present in the feedstock before and after pretreatment It appears that the content of sulfur-comprising compounds in the ethanol feedstock pretreated on the acidic resin remains high (65.5 ppm by weight of sulfur). In contrast, the nitrogen content is greatly reduced after the pretreatment on the acidic resin.

In addition, during this pretreatment, a portion of the ethanol is converted into diethyl ether (DEE).

The pretreated feedstock is then partially vaporized. The pressure of the pretreated ethanol feedstock at the inlet of the partial vaporization section is 0.45 MPa. A gaseous stream corresponding to 81.2% by weight of the pretreated ethanol feedstock introduced into the flash vessel is recovered at the top of the flash vessel and 18.8% by weight of the vaporization feedstock is recovered in liquid form at the bottom of the flash vessel. The characteristics of the vaporized ethanol feedstock (gaseous stream) and of the liquid stream which are recovered are presented in table 7.

TABLE 7

Characteristics of the pretreated ethanol feedstock and of the gaseous
(vaporized feedstock) and liquid (liquid stream) streams after
partial vaporization

|  | PRETREATED<br>ETHANOL<br>FEEDSTOCK | VAPORIZED<br>ETHANOL<br>FEEDSTOCK | LIQUID<br>STREAM |
|---|---|---|---|
| ETHANOL (% by weight) | 78.9% | 83.9% | 57.3% |
| H$_2$O (% by weight) | 12.0% | 7.0% | 33.7% |
| DEE (% by weight) | 8.8% | 9.1% | 7.5% |
| NITROGEN* (ppm by weight) | 0.6 ppm | 0.7 ppm | <0.5 ppm |
| SULFUR** (ppm by weight) | 65.5 ppm | 1.2 ppm | 343 ppm |

*content of elemental nitrogen provided by the nitrogen-comprising compounds present
**content of elemental sulfur provided by the sulfur-comprising compounds present It is clearly apparent that the majority of the sulfur-comprising impurities of the pretreated ethanol feedstock are found in the liquid stream recovered at the bottom of the flash vessel: approximately 98.5% by weight (i.e. (18.8%× 343)/65.5) of the sulfur of the pretreated feedstock is found in the liquid stream and only about 1.5% by weight (i.e. (81.2%×1.2)/65.5) of the sulfur from the pretreated feedstock is found in the gaseous stream recovered at the top.

The nitrogen and sulfur contents of the vaporized ethanol feedstock, recovered after the sequence of the pretreatment on resin and then the partial vaporization, are low: the nitrogen content of the vaporized ethanol feedstock is 0.7 ppm by weight and the sulfur content of the vaporized ethanol feedstock is 1.2 ppm by weight, relative to the total weight of said vaporized ethanol stream.

Purification Stage d)

The liquid stream is sent to a stripper (or a distillation column without reflux) to produce an ethanol stream recovered at the top of the column, a water stream and a residue recovered at the bottom of the column.

Use of the Gaseous Stream: Dehydration Stage

The vaporized feedstock is sent to the dehydration section. The dehydration reaction is carried out in a pilot-sized fixed-bed reactor. The catalyst used is that used for the dehydration of ethanol as described in patent WO 2013/011208. This comprises 80% by weight of ZSM-5 zeolite treated with H3PO4 so that the phosphorus P content is 3% by weight. For the purposes of the tests, the catalyst was ground.

The operating conditions are as follows: HSVtotal=21 h$^{-1}$ (HSV for hourly space velocity, defined as the ratio of the hourly volume flow rate of the introduced feedstock to the volume of catalyst), P=0.2 MPa. The temperature of the reaction is adjusted in order to achieve a conversion of greater than 99.9% of the ethanol in the feedstock used.

The test starts with a mixture of 90% by weight of pure ethanol and 10% by weight of pure water, in order to create a reference. After 48 hours of stabilization, the vaporized feedstock recovered previously is injected, and then the (untreated) phlegm ethanol is injected in turn.

Table 8 shows the temperatures necessary to achieve the 99.9% conversion of the ethanol in the feedstock introduced into the reactor.

TABLE 8

Reaction temperatures in the presence of pure ethanol + 10% by weight of water, of the vaporized feedstock and of the phlegm ethanol (HSV = 21 h$^{-1}$, P = 0.2 MPa)

| | PURE ETHANOL + 10 wt % of WATER | VAPORIZED ETHANOL FEEDSTOCK | PHLEGM ETHANOL |
|---|---|---|---|
| Temperature (° C.) | 400° C. | 400° C. | 445° C. |

It appears that, in the presence of the vaporized feedstock recovered at the end of the treatment according to the invention, the temperature for achieving a conversion of 99.9% is not changed compared to a reference pure ethanol feedstock. In contrast, when the ethanol introduced is the (untreated) phlegm ethanol, it is necessary to increase the temperature by 45° C. to maintain a conversion of 99.9%. Thus, the lifetime of the dehydration catalyst will be extended when the ethanol feedstock is treated by the process according to the invention, compared to the crude ethanol feedstock (phlegm ethanol).

The comparison of the tests described in example 1 (treated ethanol feedstock resulting from the fermentation of wheat according to a process of dry milling type) and in example 3 (treated ethanol feedstock=phlegm ethanol) demonstrates that the treatment process according to the invention makes it possible to diversify the source of the ethanol feedstock for the dehydration.

Example 4: Not in Accordance with the Invention

Example 4 illustrates the effect on the dehydration reaction of a process for treating the ethanol feedstock comprising only the partial vaporization stage (not in accordance with the invention).

In this example, the ethanol feedstock under consideration is the same as that of example 3: phlegm ethanol.

The ethanol feedstock is sent to a partial vaporization section, at an inlet pressure of 0.45 MPa. The temperature is adjusted so as to produce a gaseous stream corresponding to 82.7% by weight of the weight of the ethanol feedstock and a liquid stream corresponding to 17.3% by weight of the weight of the ethanol feedstock at the bottom of the flash vessel. The characteristics of the gaseous and liquid streams recovered are presented in table 9.

TABLE 9

Characteristics of the crude ethanol feedstock (phlegm ethanol) and of the gaseous and liquid streams obtained after partial vaporization

| | PHLEGM ETHANOL | GASEOUS STREAM | LIQUID STREAM |
|---|---|---|---|
| ETHANOL (% by weight) | 89.8% | 91.7% | 80.7% |
| H$_2$O (% by weight) | 9.9% | 8.3% | 17.5% |
| DEE (% by weight) | not detected | not detected | not detected |
| NITROGEN* (ppm by weight) | 3.2 ppm | 2.9 ppm | 4.6 ppm |
| SULFUR** (ppm by weight) | 64 ppm | 4.1 ppm | 348 ppm |

*content of elemental nitrogen provided by the nitrogen-comprising compounds present
**content of elemental sulfur provided by the sulfur-comprising compounds present As described in example 3, the gaseous stream obtained is sent to a dehydration section and is tested under similar conditions:

The dehydration reaction is carried out in a pilot-sized fixed-bed reactor. The catalyst used comprises 80% by weight of ZSM-5 zeolite treated with H$_3$PO$_4$ so that the phosphorus P content is 3% by weight. The catalyst was ground prior to the test.

The operating conditions are as follows: HSVtotal=21 h$^{-1}$ (HSV for hourly space velocity, defined as the ratio of the hourly volume flow rate of the introduced feedstock to the volume of catalyst), P=0.2 MPa. The temperature of the reaction is adjusted in order to achieve a conversion of greater than 99.9% of the ethanol in the feedstock used.

The test starts with a mixture of 90% by weight of pure ethanol and 10% by weight of pure water, in order to create a reference. After 48 hours of stabilization, the gaseous stream recovered previously is injected, and then the phlegm ethanol (i.e. the crude ethanol feedstock) is injected in turn.

Table 10 shows the temperatures necessary to achieve the 99.9% conversion of the ethanol in the feedstock introduced into the reactor.

TABLE 10

Reaction temperatures in the presence of pure ethanol + 10% by weight of water, of the gaseous stream obtained and of the phlegm ethanol (HSV = 21 h$^{-1}$, P = 0.2 MPa)

| | PURE ETHANOL + 10 wt % of WATER | GASEOUS STREAM | PHLEGM ETHANOL |
|---|---|---|---|
| Temperature (° C.) | 400° C. | 438° C. | 445° C. |

In the presence of the gaseous stream recovered at the outlet of the partial vaporization section, described in example 4 (not in accordance), that is to say after treatment of the ethanol feedstock comprising only partial vaporization (no pretreatment on acidic solid), the dehydration temperature to achieve 99.9% conversion is increased (+38° C.) compared to the reference test (pure ethanol with 10% water) and compared to the vaporized ethanol feedstock recovered as described in example 3 (in accordance), that is to say after treatment of the ethanol feedstock comprising a pretreatment on acidic resin and partial vaporization. Even if this increase in reaction temperature is less compared to the test carried out in the presence of phlegm ethanol (+45° C.), it remains indicative of a premature deactivation of the dehydration catalyst.

Example 5: Not in Accordance with the Invention

Example 5 illustrates the effect on the dehydration reaction of a process for treating the ethanol feedstock comprising only the pretreatment on resin (not in accordance with the invention).

The ethanol feedstock under consideration is produced by the fermentation of wheat. This is the phlegm (or phlegm ethanol), i.e. the crude ethanol obtained after a simple distillation.

As described in example 3, the ethanol feedstock (or phlegm ethanol) is preheated to 135° C., and then is pretreated on a TA801 resin (from Axens). During this pretreatment, the temperature is 135° C. and the pressure is maintained at 0.5 MPa. The (untreated) phlegm ethanol and the pretreated ethanol feedstock have characteristics similar to those given in table 6.

The pretreated ethanol feedstock is sent directly to the dehydration section for testing.

The test parameters are the same as those described in examples 3 and 4 (catalyst, P, HSV).

Similarly, the test starts with a mixture of 90% by weight of pure ethanol and 10% by weight of pure water, in order to create a reference. After 48 hours of stabilization, the ethanol feedstock pretreated on resin is injected. The temperature of the reaction is adjusted in order to achieve a conversion of greater than 99.9% of the ethanol in the feedstock introduced into the reactor. Table 11 shows the temperatures necessary to achieve the 99.9% conversion of the ethanol in the feedstock introduced into the reactor.

TABLE 11

Reaction temperatures in the presence of pure ethanol + 10% by weight of water and of the pretreated feedstock (HSV = 21 h$^{-1}$, P = 0.2 MPa)

|  | PURE ETHANOL + 10 wt % of WATER | PRETREATED ETHANOL FEEDSTOCK |
| --- | --- | --- |
| Temperature (° C.) | 400° C. | 430° C. |

When the ethanol feedstock, derived from the phlegm ethanol, only undergoes the stage of pretreatment on resin, it is necessary to increase the temperature by 30° C. in order to achieve the 99.9% conversion. This increase is certainly less than with the untreated phlegm ethanol (+45° C. according to table 8) but remains substantial and significantly reduces the lifetime of the dehydration catalyst.

The invention claimed is:

1. A process for treating an alcoholic feedstock containing at least one monoalcohol, comprising the following stages:
   a) a stage of preheating of said alcoholic feedstock to a temperature of between 70° C. and 200° C., to produce a preheated alcoholic feedstock;
   b) a stage of pretreatment of said preheated alcoholic feedstock on an acidic solid, operating at a temperature of between 70° C. and 200° C., to produce a pretreated alcoholic feedstock;
   c) a stage of partial vaporization of a vaporization feedstock to produce a gaseous stream and a liquid stream, said vaporization feedstock comprising said pretreated alcoholic feedstock obtained at the end of stage b), said partial vaporization stage comprising a partial vaporization section fed with said vaporization feedstock at an inlet pressure of between 0.1 and 1.4 MPa, to produce said gaseous stream and said liquid stream such that the gaseous stream represents at least 70% by weight of the weight of the vaporization feedstock;
   d) a stage of purification of the liquid stream resulting from stage c), to give a stream rich in water, a stream rich in monoalcohol and a stream rich in impurities.

2. The treatment process as claimed in claim 1, wherein said alcoholic feedstock is an alcohol feedstock produced from renewable resources derived from biomass.

3. The treatment process as claimed in claim 1, wherein said monoalcohol is selected from ethanol, n-propanol, isopropanol, isobutanol, and mixtures thereof.

4. The treatment process as claimed in claim 1, wherein pretreatment stage b) is operated at a temperature of between 100° C. and 180° C.

5. The treatment process as claimed in claim 1, wherein said acidic solid is chosen from acidic clays, zeolites, sulfated zirconias, and acidic resins.

6. The treatment process as claimed in claim 5, wherein said acidic solid is an acidic resin which possesses an exchange capacity of at least 0.1 mmol H$^+$ equivalent per gram.

7. The treatment process as claimed in claim 1, wherein the water content of the vaporization feedstock is between 10% and 75% by weight of water relative to the total weight of the vaporization feedstock.

8. The treatment process as claimed in claim 1, wherein said vaporization feedstock additionally comprises a recycled stream of water purified according to stage d) and/or a stream of external water.

9. The treatment process as claimed in claim 1, wherein said partial vaporization section comprises a heat exchanger and a flash evaporator.

10. The treatment process as claimed in claim 1, wherein said partial vaporization section is fed with said vaporization feedstock at an inlet pressure of between 0.2 and 0.6 MPa.

11. The treatment process as claimed in claim 1, wherein the gaseous stream resulting from said partial vaporization section represents at least 80% by weight of the weight of the vaporization feedstock.

12. The treatment process as claimed in claim 1, wherein the gaseous stream represents a proportion of 70% by weight to 98% by weight of the weight of the vaporization feedstock.

13. The treatment process as claimed in claim 1, wherein the temperature of said vaporization feedstock is adjusted in said partial vaporization section to a temperature of between 110° C. and 250° C.

14. The treatment process as claimed in claim 1, wherein, during said purification stage d), said liquid stream resulting from stage c) is purified by stripping.

15. The treatment process as claimed in claim 1, wherein said stream rich in said monoalcohol recovered at the top of the purification section of said stage d) is at least partially recycled and mixed with the gaseous stream obtained at the end of stage c).

16. The treatment process as claimed in claim 1, wherein at least a portion of said stream of purified water resulting from stage d) is recycled to the inlet of stage c) and mixed with the pretreated alcoholic feedstock obtained at the end of pretreatment stage b) to produce the vaporization feedstock, and/or recycled to the outlet of stage c) and mixed with the gaseous stream obtained at the end of said partial vaporization stage c).

17. The treatment process as claimed in claim 1, wherein said alcoholic feedstock is an alcohol feedstock produced by fermentation of biomass.

18. The treatment process as claimed in claim 1, wherein pretreatment stage b) is operated at a temperature of between 110° C. and 160° C.

19. The treatment process as claimed in claim 5, wherein said acidic solid is a cation exchange resin which possesses an exchange capacity of at least 0.1 mmol $H^+$ equivalent per gram.

20. The treatment process as claimed in claim 1, wherein the gaseous stream resulting from said partial vaporization section represents at least 90% by weight of the weight of the vaporization feedstock.

21. The treatment process as claimed in claim 1, wherein the gaseous stream represents a proportion of 70% by weight to 95% by weight of the weight of the vaporization feedstock.

* * * * *